US00PP14885P2

(12) United States Plant Patent
Pomeroy et al.

(10) Patent No.: US PP14,885 P2
(45) Date of Patent: Jun. 8, 2004

(54) CROCOSMIA PLANT NAMED 'CROPOM'

(50) Latin Name: *Crocosmia masonorum×crocosmiiflora*
Varietal Denomination: Cropom

(75) Inventors: Kevin Pomeroy, Clonee (IE); Paul Gooderham, Diss (GB)

(73) Assignee: Blooms of Bressingham Ltd., Bressingham (GB)

( * ) Notice: Subject to any disclaimer, the term of this patent is extended or adjusted under 35 U.S.C. 154(b) by 0 days.

(21) Appl. No.: 10/602,090

(22) Filed: Jun. 23, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A distinct cultivar of Crocosmia plant named 'Cropom', characterized by its upright and somewhat outwardly arching plant habit; freely flowering habit; and large yellow and red bi-colored flowers that face mostly upright.

1 Drawing Sheet

Botanical classification/cultivar designation: *Crocosmia masonorum×crocosmiiflora* cultivar Cropom.

BACKGROUND OF THE INVENTION

The present Invention relates to a new and distinct cultivar of Crocosmia plant, botanically known as *Crocosmia masonorum×crocosmiiflora,* and hereinafter referred to by the cultivar name 'Cropom'.

The new Crocosmia is the product of a planned breeding program conducted by the Inventors in County Meath, Ireland. The purpose of the breeding program is to create new Crocosmia cultivars with larger and more open flowers that are held upright on the plant.

The new Crocosmia originated from a cross-pollination of an unnamed selection of *Crocosmia masonorum,* not patented, as the female, or seed, parent, with an unnamed selection of *Crocosmia crocosmiiflora,* not patented, as the male, or pollen, parent. The cultivar Cropom was discovered and selected by the Inventors as a flowering plant within the progeny of the stated cross-pollination in a controlled environment in 1997 in County Meath, Ireland.

Asexual reproduction of the new cultivar by divisions of corms taken at Bressingham, United Kingdom, since the autumn of 1998, has shown that the unique features of this new Crocosmia are stable and reproduced true to type in successive generations.

SUMMARY OF THE INVENTION

Plants of the cultivar Cropom have not been observed under all possible environmental conditions. The phenotype may vary somewhat with variations in environment such as temperature and light intensity without, however, any variance in genotype.

The following traits have been repeatedly observed and are determined to be the unique characteristics of 'Cropom'. These characteristics in combination distinguish 'Cropom' as a new and distinct cultivar:

1. Upright and somewhat outwardly arching plant habit.
2. Freely flowering habit.

3. Large yellow and red bi-colored flowers that face mostly upright.

Plants of the new Crocosmia differ from plants of the parent selections primarily in flower color as plants of the female parent selection have orange red-colored flowers and plants of the male parent selection have yellow-colored flowers. In addition, flowers of plants of the new Crocosmia are more upright-facing than flowers of plants of the parent selections.

Plants of the new Crocosmia can be compared to plants of the Crocosmia cultivar Pomry, not patented. In side-by-side comparisons conducted in County Meath, Ireland, plants of the new Crocosmia differed from plants of the cultivar Pomry primarily in flower color as plants of the cultivar Pomry had bright red-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new Crocosmia.

The photograph at the top of the sheet comprises a side perspective view of a typical plant of 'Cropom' grown in a container.

The photograph on at the bottom of the sheet comprises a close-up view of typical flowers of 'Cropom'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown in Mount Vernon, Wash. under outdoor field conditions which closely approximate commercial production conditions. During the production of the plants, day temperatures ranged from 10 to 28° C. and night temperatures ranged from 2 to 15° C. Plants used for the photographs and description were grown for one growing season in containers.

Botanical classification: *Crocosmia masonorum*× *crocosmiiflora* cultivar Cropom.

Parentage:

*Female, or seed, parent.*—Unnamed selection of *Crocosmia masonorum,* not patented.

*Male, or pollen, parent.*—Unnamed selection of *Crocosmia crocosmiiflora,* not patented.

Propagation:

*Type.*—By divisions of corms.

*Time to initiate roots.*—About 10 days at 20° C.

*Time to produce a rooted cutting.*—About 30 days at 20° C.

*Root description.*—Fibrous, thin, grayed white in color.

*Rooting habit.*—Freely branching, dense.

*Corms.*—Height: About 2.5 cm. Diameter: About 4.5 cm. Shape: Oblate. Texture: Fleshy. Color: 174B to 174C.

Plant description:

*Plant form.*—Upright and somewhat outwardly spreading perennial; leaves and flowering stems, basal.

*Plant height, soil level to top of flowers.*—About 50 cm.

*Plant width or spread.*—About 63 cm.

*Foliage description.*—Arrangement: Simple; basal; sessile, clasping. Length: About 35 cm. Width: About 2.6 cm. Shape: Linear. Apex: Sharply acute to acuminate. Base: Clasping. Margin: Entire. Texture, upper and lower surfaces: Smooth, glabrous. Venation pattern: Parallel. Color: Developing and fully expanded foliage, upper surface: Closest to 147A. Developing and fully expanded foliage, lower surface: Closest to 147A. Venation, upper and lower surfaces: Closest to 147A.

Flower description:

*Flower type and habit.*—Single salverform flowers arranged on terminal and lateral spikes. Typically one terminal spike with two or three lateral spikes. Flowering stems, erect to slightly outwardly spreading; flowers face mostly upright. Flowers persistent.

*Fragrance.*—None detected.

*Natural flowering season.*—Continuously flowering during the spring.

*Quantity.*—Freely flowering with about 17 flowers per terminal spike and about 11 flowers per lateral spike.

*Flower longevity.*—Individual flowers last about two days on the plant, inflorescences last about one to two weeks on the plant.

*Inflorescence length.*—Terminal spikes, about 13 cm; lateral spikes, about 8 cm.

*Inflorescence width.*—Terminal spikes, about 9 cm; lateral spikes, about 7.5 cm.

*Flower diameter.*—About 4.5 cm.

*Flower depth* (*height*).—About 2.3 cm.

*Flower throat diameter.*—About 4 mm.

*Flower tube length.*—About 1.8 cm.

*Flower tube diameter, base.*—About 2 mm.

*Flower buds* (*just before opening*).—Length: About 1.75 cm. Diameter: About 3 mm. Shape: Oblong. Color: 17A; towards the apex, 45A.

*Perianth segments.*—Quantity/arrangement: Six petal-like segments fused into a tube that flare outwardly. Length from tube: About 1.7 cm. Width: About 1 cm. Shape: Roughly elliptic. Apex: Acute and emarginate. Margin: Entire. Texture, upper and lower surfaces: Smooth; satiny. Color: When opening and fully opened, upper surface: More yellow than 12A; towards the apex, 45A; two nectar stripes towards segment base, 45A. When opening and fully opened, lower surface: Close to 15A; towards the apex, 45A.

*Spathe valve.*—Quantity/arrangement: Two, imbricate. Length: About 1.3 cm. Diameter: About 1.2 cm. Shape: Narrowly deltoid. Apex: Acute. Base: Truncate. Margin: Entire. Texture, upper and lower surfaces: Smooth, glabrous. Color, upper surface: 144A underlain with 187A. Color, lower surface: 144A infused with 187A.

*Flowering stems.*—Length: About 65 cm. Diameter: About 4 mm. Strength: Moderately strong. Angle: Mostly erect; slightly bending with weight of flowers. Texture: Smooth, glabrous. Color: Close to 147A.

*Reproductive organs.*—Stamens: Quantity per flower: Two. Filament length: About 3.7 cm. Filament color: 7A. Anther size: About 7.5 mm by less than 1 mm. Anther shape: Linear. Anther color: 9A. Pollen amount: Moderate. Pollen color: 9A. Pistils: Quantity per flower: One. Style length: About 4.4 cm. Style color: 7A. Stigma shape: Triangular. Stigma color: 7A. Ovary color: Close to 151A.

*Seed/fruit.*—Seed and fruit production have not been observed.

Disease/pest resistance: Under commercial production conditions, plants of the new Crocosmia have not been noted to be resistant to pathogens or pests common to Crocosmia.

Weather/temperature tolerance: Plants of the new Crocosmia have been observed to tolerate rain, wind, and temperatures from −8 to 40° C.

It is claimed:

1. A new and distinct cultivar of Crocosmia plant named 'Cropom', as illustrated and described.

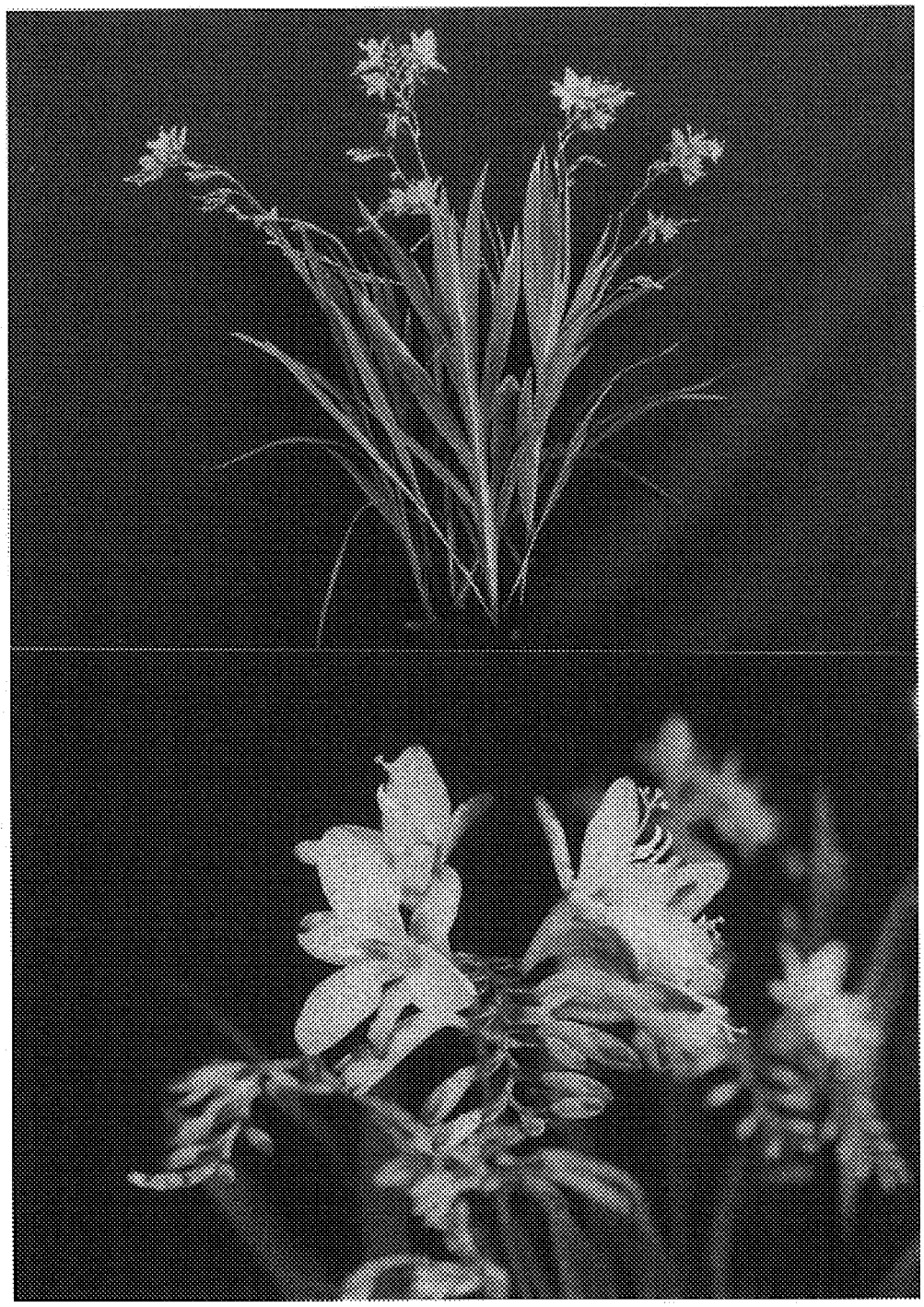

* * * * *